(12) United States Patent
Aono (10) Patent No.: US 9,247,213 B2
(45) Date of Patent: Jan. 26, 2016

(54) APPARATUS FOR DETECTING DEFECT OF WORK

(75) Inventor: Hiroshi Aono, Miyoshi (JP)

(73) Assignee: TOYOTA JIDOSHA KABUSHIKI KAISHA, Toyota-Shi (JP)

( * ) Notice: Subject to any disclaimer, the term of this patent is extended or adjusted under 35 U.S.C. 154(b) by 316 days.

(21) Appl. No.: 14/006,435

(22) PCT Filed: Mar. 23, 2011

(86) PCT No.: PCT/JP2011/057007
§ 371 (c)(1),
(2), (4) Date: Sep. 20, 2013

(87) PCT Pub. No.: WO2012/127657
PCT Pub. Date: Sep. 27, 2012

(65) Prior Publication Data
US 2014/0015961 A1 Jan. 16, 2014

(51) Int. Cl.
*H04N 7/18* (2006.01)
*G01N 21/95* (2006.01)
*G01N 21/952* (2006.01)

(52) U.S. Cl.
CPC .............. *H04N 7/18* (2013.01); *G01N 21/952* (2013.01); *G01N 21/9515* (2013.01)

(58) Field of Classification Search
CPC .... G01N 21/9515; G01N 21/952; H04N 7/18
USPC ........................................................ 348/128
See application file for complete search history.

(56) References Cited

U.S. PATENT DOCUMENTS

| | | | | | |
|---|---|---|---|---|---|
| 4,226,539 | A | * | 10/1980 | Nakagawa | G01N 21/952 250/559.39 |
| 4,410,278 | A | * | 10/1983 | Makihira | G01N 21/952 250/559.07 |
| 5,392,359 | A | * | 2/1995 | Futamura | G06T 7/0006 348/128 |
| 5,602,646 | A | * | 2/1997 | Bernardin | G01N 21/952 356/237.2 |
| 7,596,248 | B2 | * | 9/2009 | Cova | G06K 9/00067 382/100 |
| 8,306,308 | B2 | * | 11/2012 | Choi | G01N 21/952 356/601 |

(Continued)

FOREIGN PATENT DOCUMENTS

| | | |
|---|---|---|
| CN | 101034070 A | 9/2007 |
| JP | 01277743 A | 11/1989 |

(Continued)

*Primary Examiner* — Jay Patel
*Assistant Examiner* — Francis G Geroleo
(74) *Attorney, Agent, or Firm* — Kenyon & Kenyon LLP (57) ABSTRACT

A defect detecting apparatus detects a defect that is present on the outer circumferential surface of work having the outer circumferential surface thereof formed as a bent surface. The defect detecting apparatus is provided with: a jig which supports the work, and holds the work in a state wherein the work is rotated by a predetermined angle; an image pickup device, which picks up an image of the outer circumferential surface of the work held by the jig, the work being in the state wherein the work is rotated by the predetermined angle; and a controller, which processes an image obtained by means of the image pickup device, and determines a defect. The controller stores information relating to the shape of the outer circumferential surface of the work, and information relating to the positional relationship, at each rotation angle, between the image pickup device and a work area having the image thereof picked up by the image pickup device, and the control apparatus uses the information at the time of determining the defect.

3 Claims, 6 Drawing Sheets

(56) References Cited

U.S. PATENT DOCUMENTS

2007/0211240 A1 9/2007 Matsumoto et al.
2010/0111367 A1* 5/2010 Hiraoka ............. G01B 11/2522
                                                  382/106

FOREIGN PATENT DOCUMENTS

| JP | 03293542 A | 12/1991 |
| JP | 04132906 A | 5/1992 |
| JP | 05180777 A | 7/1993 |
| JP | 0820369 B2 | 3/1996 |
| JP | 2000121569 A | 4/2000 |
| JP | 2001242095 A | 9/2001 |
| JP | 2002098643 A | 4/2002 |
| JP | 2008076320 A | 4/2008 |
| JP | 2008233106 A | 10/2008 |

* cited by examiner

APPARATUS FOR DETECTING DEFECT OF WORK

CROSS REFERENCE TO RELATED APPLICATION

This is a national phase application based on the PCT International Patent Application No. PCT/JP2011/057007 filed on Mar. 23, 2011, the entire contents of which are incorporated herein by reference.

TECHNICAL FIELD

The present invention relates to a technique of detecting defects of the outside of a work.

BACKGROUND ART

JP H03-293542 A discloses a technique of inspecting defects of the surface of a camshaft. In the technique of JP H03-293542 A, the cam surface is divided into multiple inspection sections considering the use of the cam, and special optical instruments are used for each of the inspection sections. Therefore, the best inspection condition for the camshaft as an object to be inspected can be chosen by changing the criterion for determining the defects in accordance with the inspection sections. Thus, the technique provides the defect inspection considering working condition or unique characteristics of the object.

JP 2008-233106 A discloses a technique of inspecting defects of the surface of a work including curved surface at the periphery thereof. In the technique of JP 2008-233106 A, conditions for an image processing are changeable in response to light and shade in the curved surface which is inclined against the imaging device, so that the defects on the curved surface can be detected.

Unfortunately, the conventional techniques do not adequately take into account the image distortion occurred in the image of the curved portion, and thus the shape, especially dimension, of the defect in the curved portion may be misdetected. Moreover, the image distortion may be occurred according to the positional relationship, such as distance or angle, between the camera for picking up the image and the work, so that it is difficult to accurately detect the defects.

CITATION LIST

Patent Literature

PTL 1: JP H03-293542 A
PTL 2: JP 2008-233106 A

SUMMARY OF INVENTION

Technical Problem

The objective of the present invention is to provide a technique of improving accuracy for detecting defects of the outer surface of a work.

Technical Solutions

The first aspect according to the invention relates to an apparatus for detecting a defect including a jig for supporting the work and holding the work rotated at predetermined angles; an image pickup device for taking images of the outer surface of the work which is held at each of the predetermined rotation angles by the jig; and a controller for processing the images obtained by the image pickup device and detecting the defect, wherein the controller stores information about a shape of the outer surface of the work and about a positional relationship between the image pickup device and an imaging area of the work taken by the image pickup device at each of the predetermined rotation angles, and uses the information to determine the defect.

In a preferable embodiment of the invention, the controller compares a magnitude of the defect included in the images taken by the image pickup device with a threshold to determine the defect.

In one embodiment, the threshold for the use of the determination is changed in response to an image distortion caused by a position of the defect in the image and by a shape of the outer surface of the work in each of the predetermined rotation angles of the work, by using the information about the shape of the outer surface of the work and about the positional relationship between the image pickup device and the imaging area of the work taken by the image pickup device at each of the predetermined rotation angles.

Furthermore, a view angle of the image pickup device is set larger than the rotation angle of the work to generate duplicate areas in the images taken by the image pickup device, and if the defect appears in two images having common duplicate area, the determination of the defect is performed by using one image of two images in which a distance between an end of the image and the defect is larger than the other image.

In an alternative embodiment, an image distortion in the images taken by the image pickup device caused by a shape of the outer surface of the work is corrected by using the information about the shape of the outer surface of the work and about the positional relationship between the image pickup device and the imaging area of the work taken by the image pickup device at each of the predetermined rotation angles, and the outer surface of the work is processed as a flat view expanded along the rotating direction by the jig, whereby the defect determination is performed using a real shape of the defect.

Advantageous Effects of Invention

According to the present invention, the accuracy for detecting the defects of the outer surface of the work can be improved.

DESCRIPTION OF EMBODIMENT

[First Embodiment]

Referring to attached drawings, a first embodiment of the present invention is described below.

A defect detecting apparatus 1 is used for detecting a defect D existing on the outer surface of a work W, in which the work W is rotated to take images of the outside and the whole outside of the work W is inspected. The defect D is a dent defect that appears on the surface of the work W, for example, a blowhole, a crack, or a scratch caused by machining. The defect D is determined whether allowable or unallowable depending on the dimension thereof, and if the defect D has the unallowable dimension, the work W is handled as a defective.

The work W has curvature along the circumference, and the outside is formed as the curved surface. The work W includes an axis R, and is configured as a shaft member being rotatable around the axis R. The work W is, for example, a column member in which the distance between the axis R and the outside is constant, or a camshaft in which the distance between the axis R and the outside is variable depending on the angle. The work W may be a square column member having flat outsides, which is rotatable around the axis R during the defect detection using the defect detecting apparatus 1.

Figure 1:
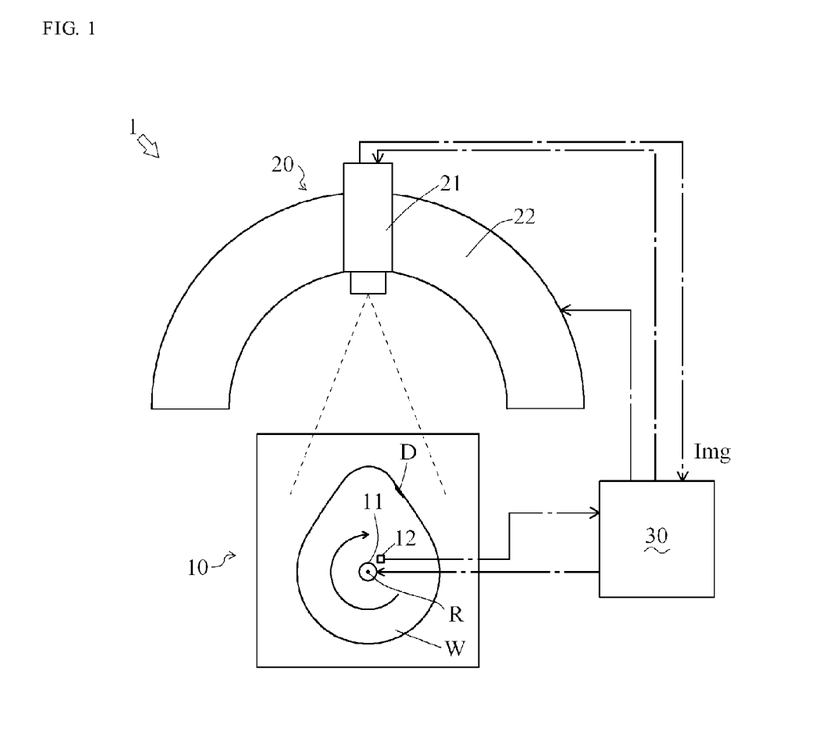
FIG. 1 depicts a defect detecting apparatus.

As shown in FIG. 1, the defect detecting apparatus 1 includes a jig 10 for supporting the work W, an image pickup device 20 for taking images of the work W, and a controller 30 for processing the images taken by the image pickup device 20 and for determining the existence of the defect D.

The jig 10 holds the work W at the predetermined position, and supports the work W rotatably around the axis R. The jig 10 contains a motor 11 for rotating the work W.

The output shaft of the motor 11 is connected to the axis R of the work W, and actuating the motor 11 makes the axis R of the work W rotated. The motor 11 is provided with an encoder 12 for detecting the rotation angle of the motor 11 (or of the axis R).

The motor 11 and the encoder 12 are electrically connected to the controller 30. The controller 30 transmits a control signal for actuating the motor 11, and the detection signal for the rotation angle of the motor 11 generated by the encoder 12 is transmitted to the controller 30. Thus, the controller 30 detects the inclination angle of the work W on the basis of the detection signal from the encoder 12, and transmits the control signal to the motor 11 for actuating/stopping, thereby holding the work W at a predetermined rotation angle.

The image pickup device 20 picks up images of the surface (outer periphery) of the work W, and obtains image data Img. The image pickup device 20 includes a camera 21 and a shadowless light 22.

The camera 21 takes images of the surface of the work W in the predetermined visual field range and generates the image data Img. The camera 21 is fixed in a position apart from the rotation axis R of the work W by the predetermined distance, thereby being unmovable with respect to the axis R.

The shadowless light 22 is configured as a light with a single dome, and lights up the surface of the work W. The shadowless light 22 includes multiple lights disposed surrounding the camera 21. In the image pickup device 20, the camera 21 takes the image in the state that the shadowless light 22 lights the work W, and the image data Img is obtained.

The camera 21 and the shadowless light 22 are electrically connected to the controller 30. The controller 30 transmits a control signal to control the lighting action of the shadowless light 22 and control the imaging action of the camera 21. Moreover, the image data Img obtained by the camera 21 is transmitted to the controller 30.

In the defect detecting apparatus 1, while the jig 10 holds the work W at the predetermined inclination angle, the camera 21 takes the image data Img of the work W. Thus, the jig 10 keeps securely the rotation angle of the work W, and the camera 21 shoots the work W. As the result, the distance between the camera 21 and the work W for each of the rotation angles of the work W is fixed, thereby fixing the imaging area of the image data Img at each of the rotation angles.

Shooting the work W in such condition, when the image data Img is obtained by the camera 21, the image distortion along the circumferential direction caused by the curvature of the outer surface of the work W can be taken into consideration according to the posture of the work W. Moreover, when the round portion is detected as a flat image, the distortion of the shape of the defect D included in the image data Img can be taken into consideration.

The controller 30 is electrically connected to the jig 10 and the image pickup device 20, and controls the actions of the camera 21 and the shadowless light 22 to synchronize the rotation of the work W with the imaging action of the camera 21. The controller receives the data obtained by the encoder 12 and the camera 21 (i.e., the rotation angle of the work W and the image data Img), and performs analysis and image processing based on the data.

The controller 30 stores information of the shape of the work W, more specifically, of the shape of outer surface of the work. The information of the outer shape of the work W is information about a positional relationship including the distance and the angle between the axis R of the work W and the outer surface, and in other words is information about the outer shape of the work W which is uniquely defined with respect to the axis R and the rotation angle of the work W. Furthermore, the controller 30 stores the geometrical distance, i.e., the positional relationship, between the camera 21 and the imaging area of the work W involved in the visual field range of the camera 21 in each of the rotation angles of the work W. In detail, the controller 30 stores degrees of the image distortion of all areas of the work W in the image data Img, and information about the shape distortion in accordance with the position of the defect D in the image data Img.

The controller 30 also stores a threshold Th according to the image distortion of the work W at each of the rotation angles of the work W, and determines that the work W has a defect having an impermissible size if the dimension of the defect D in the image data Img is larger than the threshold Th.

The controller 30 uses information of the outer shape of the work W and of the positional relationship between the camera 21 and the imaging area of the work W involved in the visual field range of the camera 21 in each of the rotation angles of the work W to compare the threshold Th with the dimension of the defect D for detection of the defect.

Figure 2:
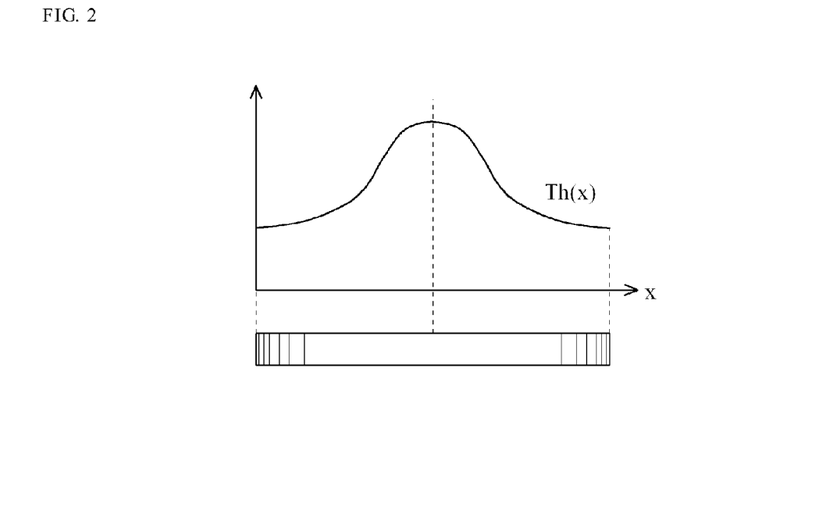
FIG. 2 shows a variation of a threshold in accordance with defect position.

The threshold Th is set in response to the magnitude of the image distortion of the image data Img. In the case that the work W is the shaft member, the threshold Th is set as a large value in a center section which faces the camera 21 and has small distortion, and is set as a small value in a side section which has larger distortion than the center section. The function threshold Th(x) is set in each of the image data Img, and as shown in FIG. 2, the threshold is a function of the position (x) in the circumferential direction in the image data Img.

Figure 3:
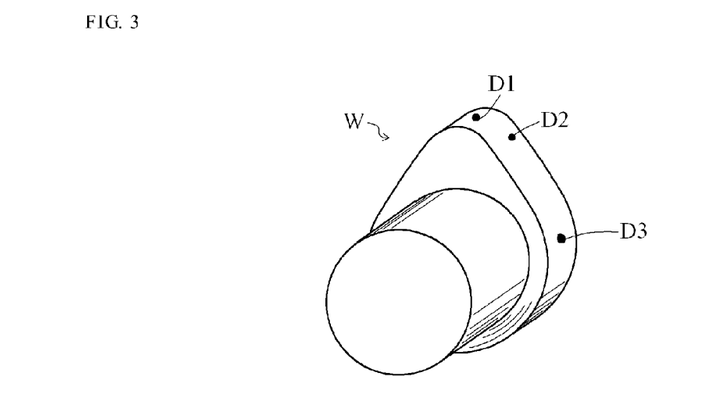
FIG. 3 depicts a work to be detected by the defect detecting apparatus.

Referring to FIGS. 3 through 6, the defect detection processing is described where the defect detecting apparatus 1 detects a work W including defects D1 to D3. As illustrated in FIG. 3, the work W is a camshaft and the defect detecting apparatus inspects the surface of a cam portion of the camshaft.

The defects D1 to D3 are typical defects supposed to exist on the cam portion of the work W. The defect D1 is a circular defect on the top, the defect D2 is a small circular defect dephased by around 40 degrees from the defect D1, and the defect D3 is a circular defect on the side. The defects D1 and D3 have the impermissible size, and the defect D2 is permissible.

Figure 4:
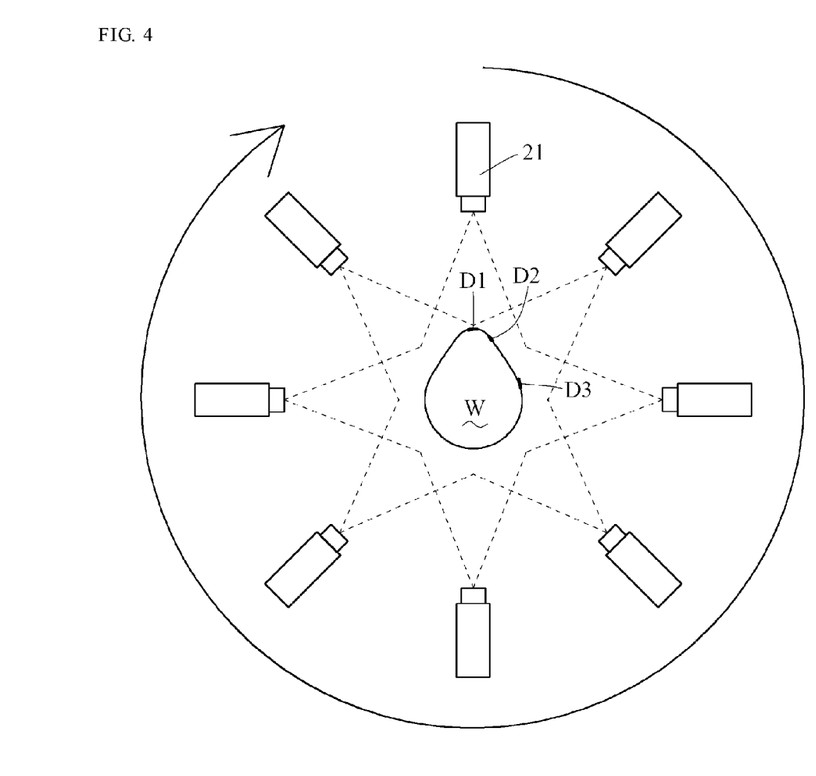
FIG. 4 illustrates an imaging action for the work using an image pickup device of the defect detecting apparatus.

As depicted in FIG. 4, the jig 10 rotates the work W by 45 degrees, and the image pickup device 20 takes eight image data Img1 to Img8. It should be noticed that FIG. 4 shows the situation that the work W is fixed and the camera 21 is rotated by 45 degrees around the axis R of the work W.

Figure 5:
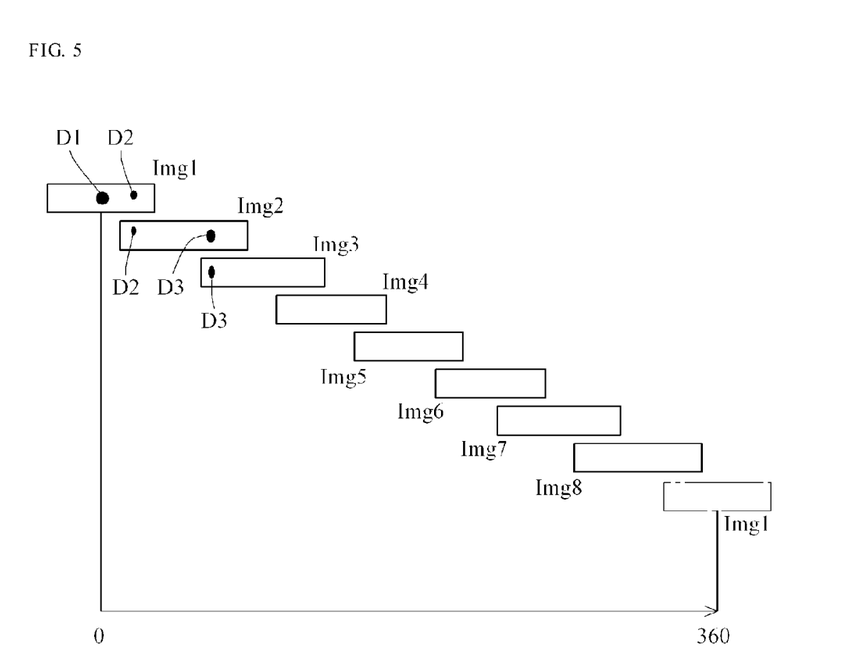
FIG. 5 shows image data taken by the image pickup device.

As shown in FIG. 5, the image pickup device 20 picks up the image data Img1 to Img8. The image data Img1 to Img8 are obtained as flat views which are taken along the circumferential direction of the outer surface of the work W in order. In FIG. 5, the circumferential direction of the work W is the left-right direction of the drawing, and the top of the cam portion of the work W is represented as an origin (O).

The controller 30 performs the detection whether the defect is allowable or unallowable by comparing the threshold Th with the position and size of the defects D1 to D3 appeared in the image data Img1 to Img8.

Figure 6:
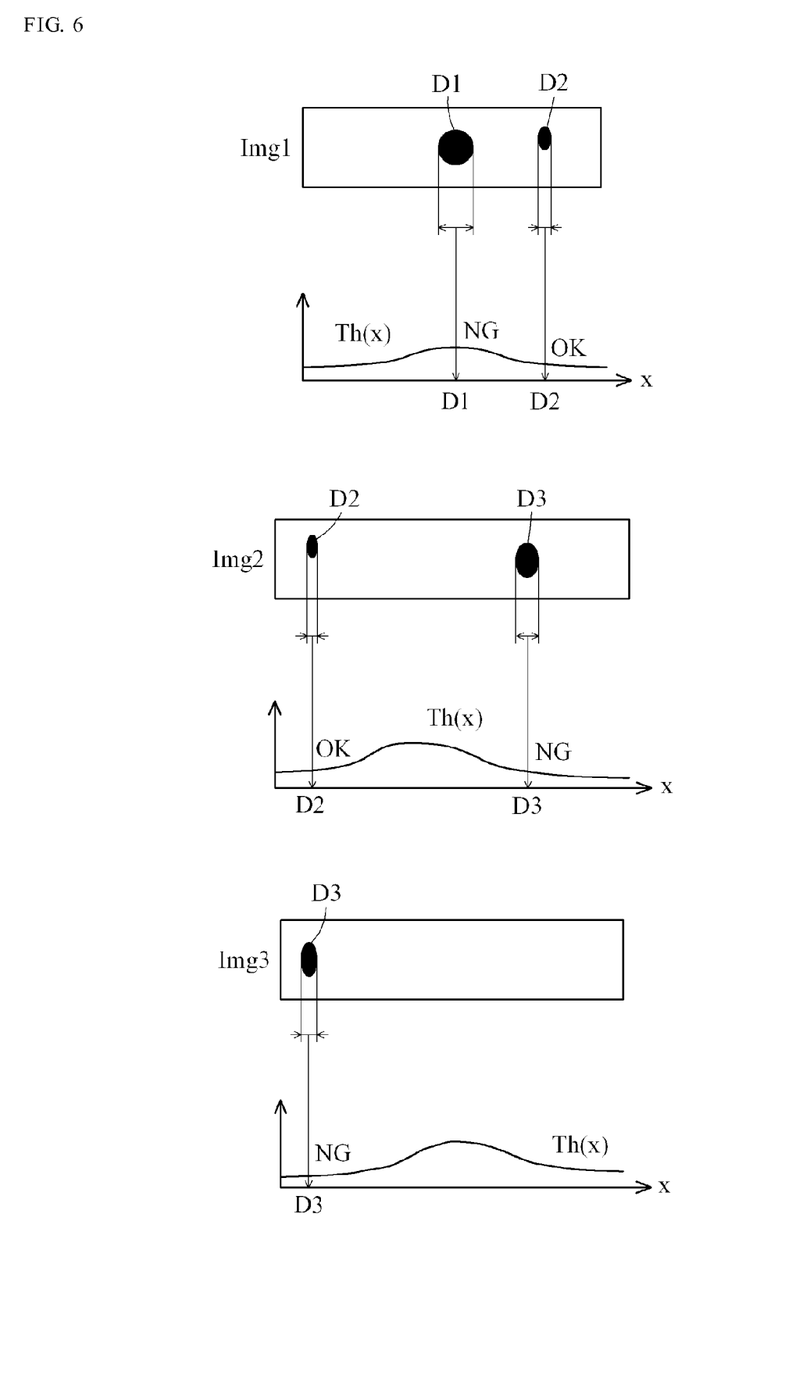
FIG. 6 shows a defect detecting processing using the image data.

As depicted in FIG. 6, considering the image distortion of each of the image data Img1 to Img8, the threshold Th(x) is set to compare the threshold Th(x) with the size of each of the defects D1 to D3 according to the position (x) in the circumferential direction of each of the defects. The defect detection is performed by comparing these values, and the magnitudes of the defects D1 and D3 have unallowable size and that of the defect D2 has allowable size.

It should be noted that the circumferential position (x) of the defect D is defined as the center position of the defect in the circumferential direction.

If the defect D has a non-circular shape such as an oval shape, a crescent shape and a curved shape, the controller 30 regards such shape as a circle, or regards the longitudinal length of the defect as a diameter of the circle on the basis of the information about the distortion in the image data Img stored in the controller, thereby detecting using the diameter and the center position.

As described above, in each of the image data Img1 to Img8, the threshold Th(x) is set in accordance with the geometrical distortion, and the position (x) and the sizes of the defects D1 to D3 included in the image are compared to the threshold Th(x). Therefore, the defect located in the outer surface of the work W having curvature, especially located at the side where the image distortion is large, can be detected with high accuracy, and therefore the reliability of the defect detecting apparatus 1 can be improved.

In this embodiment, the dimension of the defect D appeared in the image data Img is used as the net dimension, there is no need to analyze the image data Img, thereby reducing the processing load for the image processing.

If the view angle (visual field range) of the image data Img is larger than the rotation angle of the work W (45 degrees), in the series of the image data, there exist the duplicate areas in the adjacent image data. In such duplicate areas, the common defect that is located in the border area is imaged in the adjacent image data, the image data including the defect located far from the end more than the other image data is used for the detection. Therefore, the defect can be inspected at the position where the image distortion is small, and thus the accuracy for detecting the defect can be improved.

More specifically, in FIG. 5, the defect D3 appeared in the end of the image data Img2 and in the end of the image data Img3.

In such case, the distances between the center of the defect D3 (in the circumferential direction) and the end of each of the image data are measured, and the magnitude of the defect D3 is determined by using the image data which has larger distance (in the embodiment, the image data Img3), thereby reducing the influence of the image distortion on the defect D3. That is, using the image data Img in which the angle of the camera 21 is smaller, the degree of the image distortion caused by the curvature can be reduced. Thus, the defect D appeared in the image data Img can be detected with high accuracy.

[Second Embodiment]

In the first embodiment, as shown in FIG. 2, the threshold Th depends on the position (x) in the circumferential direction, in other words, the threshold Th(x) is the function of the position (x).

Figure 7:
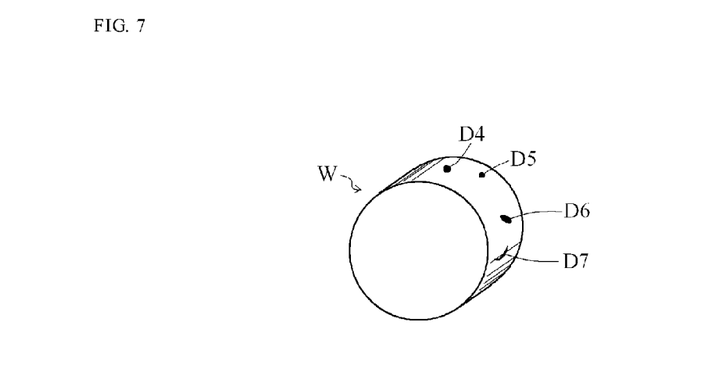
FIG. 7 illustrates a work to be detected by the defect detecting apparatus.
Figure 8:
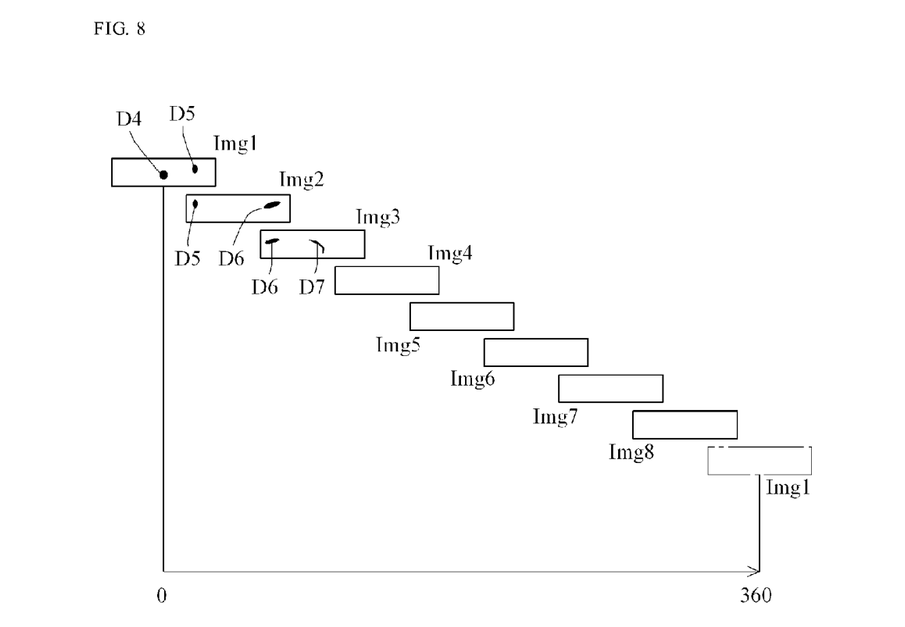
FIG. 8 shows image data taken by the image pickup device.
Figure 9:
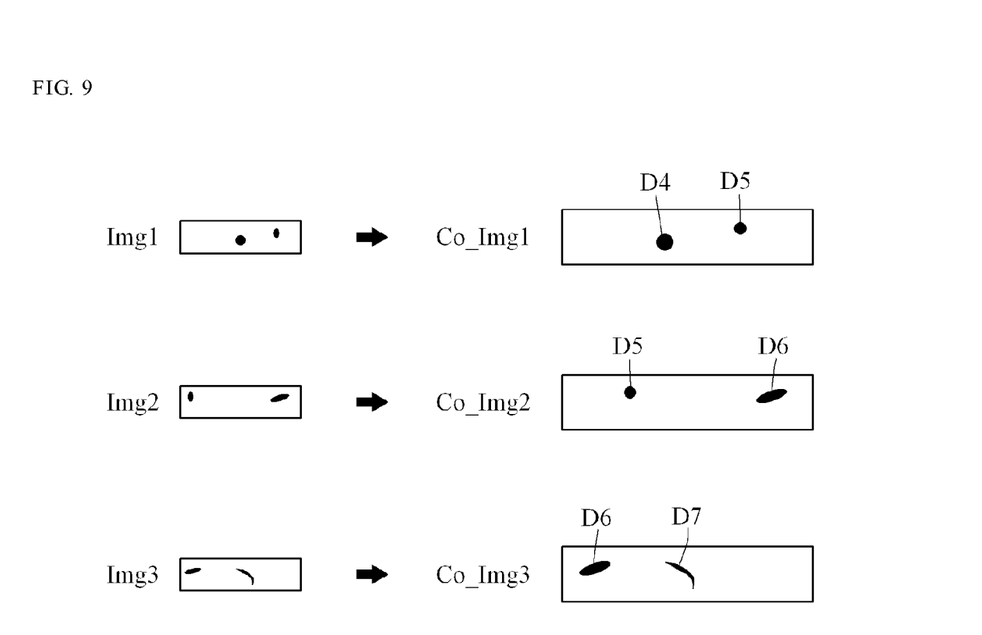
FIG. 9 shows corrected images obtained by correcting the image data.

Referring to FIGS. 7 through 9, the second embodiment of the defect detecting apparatus is described below, in which the threshold Th is a constant value. In the second embodiment, the shape of the defect D is corrected to the real shape in consideration of the image distortion, and the defect detection is performed, specifically as follows.

As depicted in FIG. 7, the work W is a column member including defects D4 to D7, and the jig 10 rotates the work W by 45 degrees and the image pickup device 20 takes the image data Img1 to Img8.

The defects D4 to D7 are typical defects supposed to exist on the surface of the work W. The defect D4 is a circular defect on the top, the defect D5 is a small circular defect dephased by around 40 degrees from the defect D4, the defect D6 is an oval defect on the side, and the defect D7 is a crescent defect on the side. The defects D4, D6 and D7 have impermissible size and the defect D5 is permissible. The defects D6 and D7 are inclined to the circumferential direction.

As shown in FIG. 8, the image pickup device 20 takes the image data Img1 to Img8.

The controller 30 corrects the image distortion of each of the image data Img1 to Img8, and takes the outer surface of the work W as a flat view expanded along the circumferential direction. In this embodiment, for recognition of the net shape of the defect D in the work W, the image data Img is processed after the correction.

In such case, the controller 30 stores information about the shape (outer shape) of the work W and about the positional relationship between the camera 21 and the imaging area of the work W involved in the visual field range of the camera 21 in each of the rotation angles of the work W, and uses the information to correct the image distortion of each of the image data Img1 to Img8.

In detail, as depicted in FIG. 9, correcting the image data Img1 to Img8 obtained by the camera 21, corrected image data Co_Img1 to Co_Img8 which have the net length in the circumferential direction of the work W in the visual field range of the camera 21 are generated.

In the corrected image data Co_Img1 to Co_Img8, the shapes of the defects D4 to D7 are shown with the net shapes thereof. So, the defect detection is carried out with comparing the threshold Th with the real magnitudes of the defects in the corrected image data Co_Img1 to Co_Img8, and thus the defects D4, D6 and D7 are determined as the unallowable defects, and the defect D5 is determined as the allowable defect.

As described above, to the image data Img1 to Img8 the geometrical image correction is performed, and the magnitudes of the defects D4 to D7 included in the corrected images are compared with the threshold Th, thereby accurately detecting the defects appeared in the outer shape of the work W having the curvature and enhancing the reliability of the defect detecting apparatus 1.

In this embodiment, the defect detection is based on the real dimension of the defect D, and therefore the defect detection can be strictly performed.

The defect presented in the work W may have a problem in the longitudinal length, so that if the defect has non-circular shape and non-oval shape, the shape of the defect is identified as an oval shape (or rectangular shape) involving the outside of the defect shape and the major axis (or long side) thereof is compared with the threshold Th for detection. As the result, a defect having variant shape can be processed in the same way.

For example, the defect D7 shown in drawings has the variant shape, or crescent shape, and in such case, the dimension of the defect is identified as the major axis of the oval involving the defect D7 or the long side of the rectangular involving the defect D7. Thus, the misjudgment caused by the shape or orientation of variant defect can be avoided.

The image pickup device 20 intermittently takes the images of the work W which is held at the predetermined angles by the jig 10. However, the image pickup device may continuously take the images with rotating the work W by the jig 10. In this case, the magnitude of the defect D can be detected where the camera 21 faces the defect D, whereby influence due to the image distortion can be reduced to a minimum.

INDUSTRIAL APPLICABILITY

The present invention can be applicable to defect inspection where the outer surface of the work has a curvature.

DESCRIPTION OF NUMERALS

1: defect detecting apparatus, 10: jig, 20: image pickup device, 30: controller, W: work, R: axis, D: defect, Img: image data

The invention claimed is:

1. An apparatus for detecting a defect in an outer surface of a work, comprising:
   a jig for supporting the work and holding the work rotated at predetermined angles;
   an image pickup device for taking images of the outer surface of the work which is held at each of the predetermined rotation angles by the jig; and
   a controller for processing the images obtained by the image pickup device and detecting the defect,
   wherein the controller stores information about a shape of the outer surface of the work and about a positional relationship between the image pickup device and an imaging area of the work taken by the image pickup device at each of the predetermined rotation angles, and compares a longitudinal dimension of the defect included in the image taken by the image pickup device with a threshold to determine the defect, and
   wherein the threshold for the use of the determination is changed in response to an image distortion caused by a position of the defect in the image and by a shape of the outer surface of the work in each of the predetermined rotation angles of the work, by using the information about the shape of the outer surface of the work and about the positional relationship between the image pickup device and the imaging area of the work taken by the image pickup device at each of the predetermined rotation angles.

2. The apparatus according to claim 1,
   wherein a view angle of the image pickup device is set larger than the rotation angle of the work to generate duplicate areas in the images taken by the image pickup device, and
   wherein if the defect appears in two images having common duplicate area, the determination of the defect is performed by using one image of two images in which a distance between an end of the image and the defect is larger than the other image.

3. An apparatus for detecting a defect in an outer surface of a work, comprising:
   a jig for supporting the work and holding the work rotated at predetermined angles;
   an image pickup device for taking images of the outer surface of the work which is held at each of the predetermined rotation angles by the jig; and
   a controller for processing the images obtained by the image pickup device and detecting the defect,
   wherein the controller stores information about a shape of the outer surface of the work and about a positional relationship between the image pickup device and an imaging area of the work taken by the image pickup device at each of the predetermined rotation angles, and compares a longitudinal dimension of the defect included in the image taken by the image pickup device with a threshold to determine the defect, and
   wherein an image distortion in the images taken by the image pickup device caused by a shape of the outer surface of the work is corrected by using the information about the shape of the outer surface of the work and about the positional relationship between the image pickup device and the imaging area of the work taken by the image pickup device at each of the predetermined rotation angles, and the outer surface of the work is processed as a flat view expanded along the rotating direction by the jig, whereby the defect determination is performed using a real shape of the defect.

* * * * *